(12) United States Patent
Grant

(10) Patent No.: US 8,287,278 B2
(45) Date of Patent: Oct. 16, 2012

(54) DENTAL IMPLANT SYSTEMS AND METHODS

(75) Inventor: James C. Grant, Colorado Springs, CO (US)

(73) Assignee: Grant Dental Technology Corporation, Colorado Springs, CO (US)

(*) Notice: Subject to any disclaimer, the term of this patent is extended or adjusted under 35 U.S.C. 154(b) by 306 days.

(21) Appl. No.: 12/694,911

(22) Filed: Jan. 27, 2010

(65) Prior Publication Data
US 2010/0159419 A1 Jun. 24, 2010

Related U.S. Application Data

(63) Continuation-in-part of application No. 12/243,676, filed on Oct. 1, 2008, now Pat. No. 8,231,388, which is a continuation-in-part of application No. 12/074,524, filed on Mar. 4, 2008, now Pat. No. 7,806,685.

(51) Int. Cl.
*A61C 8/00* (2006.01)
(52) U.S. Cl. .................................................. 433/174
(58) Field of Classification Search .......... 433/172–176, 433/201.1, 202.1, 215, 220, 221; 606/280, 606/70–71, 281–299, 86 B
See application file for complete search history.

(56) References Cited

U.S. PATENT DOCUMENTS

| | | | |
|---|---|---|---|
| 4,086,701 A | 5/1978 | Kawahara et al. | |
| 5,040,982 A | 8/1991 | Stefan-Dogar | |
| 5,297,963 A | 3/1994 | Dafatry | |
| 5,513,989 A * | 5/1996 | Crisio | 433/176 |
| 5,564,925 A | 10/1996 | Shampanier | |
| 5,591,029 A | 1/1997 | Zuest | |
| 5,810,592 A | 9/1998 | Daftary | |
| 6,068,479 A | 5/2000 | Kwan | |
| 6,120,292 A | 9/2000 | Buser et al. | |
| 6,168,436 B1 | 1/2001 | O'Brien | |
| 6,250,922 B1 | 6/2001 | Bassett et al. | |
| 6,287,117 B1 | 9/2001 | Niznick | |
| 6,454,569 B1 | 9/2002 | Hollander et al. | |
| 6,537,069 B1 | 3/2003 | Simmons, Jr. | |
| 6,843,653 B2 | 1/2005 | Carlton | |
| 6,863,529 B2 | 3/2005 | Strong et al. | |
| 7,056,117 B2 | 6/2006 | Simmons, Jr. | |
| 7,097,451 B2 | 8/2006 | Tang | |
| 7,101,177 B2 | 9/2006 | Lin | |

(Continued)

OTHER PUBLICATIONS

International Search Report and Written Opinion of PCT/US2011/022737 mailed on Mar. 23, 2011, 10 pages.

(Continued)

*Primary Examiner* — Heidi M Eide
(74) *Attorney, Agent, or Firm* — Kilpatrick Townsend & Stockton LLP

(57) ABSTRACT

A dental implant system includes a base member that is adapted to be embedded within a patient's jawbone at a treatment site. The base member has a generally flat top side defining an outer periphery, a bottom side, a central opening, and at least one screw hole positioned between the central opening and the outer periphery. The system also includes an implant screw that is adapted to pass through the central opening of the base member and into the patient's jawbone. The system further includes a securing screw that is smaller in size than the implant screw and has a head and a threaded end. The threaded end of the securing screw passes through the screw hole of the base member and into the patient's jawbone.

28 Claims, 14 Drawing Sheets

U.S. PATENT DOCUMENTS

| | | |
|---|---|---|
| 7,806,685 B1 | 10/2010 | Grant |
| 2002/0076673 A1 | 6/2002 | Wagner et al. |
| 2003/0180686 A1* | 9/2003 | Simmons, Jr. .............. 433/173 |
| 2004/0265781 A1 | 12/2004 | Coatoam |
| 2006/0014120 A1 | 1/2006 | Sapian |
| 2008/0118892 A1 | 5/2008 | Adams |
| 2008/0124675 A1 | 5/2008 | Adams |
| 2009/0226857 A1 | 9/2009 | Grant |
| 2009/0258329 A1 | 10/2009 | Adams |
| 2010/0112522 A1* | 5/2010 | Kwon ......................... 433/174 |
| 2010/0266987 A1 | 10/2010 | Ford |
| 2010/0330534 A1 | 12/2010 | Hyun |
| 2011/0118742 A1* | 5/2011 | Hulliger et al. ............... 606/70 |
| 2011/0151408 A1 | 6/2011 | Grant |

OTHER PUBLICATIONS

Plate. (n.d.), Dictionary.com Unabridged, retrieved Dec. 1, 2010 from Dictionary.com website: http://dictionary.reference.com/browse/plate, 12 pages.

Stud. (n.d.), Dictionary.com Unabridged, retrieved Apr. 20, 2011, from Dictionary.com website: http://dictionary.reference.com/browse/stud.

Teeth. (n.d.), Dictionary.com Unabridged, retrieved Apr. 20, 2011, from Dictionary.com website: http://dictionary.reference.com/browse/teeth.

* cited by examiner

DENTAL IMPLANT SYSTEMS AND METHODS

CROSS-REFERENCES TO RELATED APPLICATIONS

This application is a continuation in part application of copending U.S. application Ser. No. 12/243,676, filed Oct. 1, 2008 which is a continuation in part application of co-pending U.S. application Ser. No. 12/074,524 filed on Mar. 4, 2008. The complete disclosures of each of these applications are herein incorporated by reference.

BACKGROUND OF THE INVENTION

Implants are popular means of replacing a lost tooth. Due to their relatively low maintenance and durability people often prefer implants to bridges. Nevertheless, there is a largely undocumented body of complaints voiced to front line dentists about implants, by their patients. These complaints generally are about food impacting and accumulating around and beneath the crown portion of the implant in the enlarged periodontal gap between the implant and the adjacent teeth.

BRIEF SUMMARY OF THE INVENTION

In one embodiment, the invention provides an exemplary method for securing a dental implant (or implant screw) to a patient's jawbone. According to the method, a portion of the patient's gum is removed sufficient to expose the patient's jawbone. This may be done after the patient's tooth or other dental work has been removed. Also, a portion of the patient's jawbone is removed. The depth of bone removal may be in the range from about 1 mm to about 4 mm. A base member is positioned at the treatment site such that it is embedded within the patient's jawbone wherein the bone has been removed. The base member may have a generally flat top side defined by an outer perimeter, a tapered central opening and at least one screw hole that is positioned between the central opening and the outer perimeter. A small securing screw is placed through the screw hole and rotated until it is screwed into the patient's jawbone and a head of the securing screw is at least flush with the top side of the base member. In this way, the base member is embedded within and securely fastened to patient's jawbone. This base member will subsequently serve as a stable platform form prosthesis. An implant screw is placed through the central opening of the base member. The implant screw has a head with a tapered section and a threaded end. The implant screw is turned to secure the threaded end within the jawbone and to seat the head of the implant screw within the tapered. Opening of the base member. Once the implant screw is secured to the jawbone and appropriate healing has occurred, a prosthesis, such as a crown, may be coupled to the implant screw.

In one aspect, the base member includes two screw holes that are positioned between the outer periphery and the central opening. As one example, the base member may be generally rectangular in geometry, with the two screw holes being located in corners of the base member. This serves to further secure the base member to the patient's jawbone. Also, when the base member is rectangular, the surgeon may also surgically remove a rectangular section of the jawbone so that the base member will fit within the resulting depression in the jawbone.

In another aspect, the top side of the base member may be embedded within the jawbone such that it is generally flush with the top surface of the patient's jawbone. In a further aspect, the top side may further include at least one mutable feature that is configured to mate with a corresponding feature on a crown to ensure non-rotatable alignment of the crown with the base member. The implant screw may further include a threaded hole and the crown may include a bolt so that the bolt may be screwed into the threaded hole.

In yet another aspect, the base member may have a generally flat bottom side, and the central opening may taper inward from the top surface to the bottom surface with a constant taper. Further, the base member may have an outer periphery that tapers with a straight taper inward from the top surface to the bottom surface such that the top surface is greater in surface area than the bottom surface.

In some cases, the outer periphery of the base member may be roughened to increase the surface area of the base member. This in turn serves to enhance bone growth to the base member.

In another embodiment, the invention provides a dental implant system that comprises a base member that is adapted to be embedded within a patient's jawbone at a treatment site. The base member has a generally flat top side defining an outer periphery, a bottom side, a central opening, and at least one screw hole positioned between the central opening and the outer periphery. The system also includes an implant screw that comprises a head and a threaded end that is adapted to pass through the central opening of the base member and into the patient's jawbone. The head of the implant screw is adapted to be seated within the central opening of the base member after the threaded end is screwed into the patient's jawbone. The system further includes a securing screw that is smaller in size than the implant screw and has a head and a threaded end. The threaded end of the securing screw passes through the screw hole of the base member and into the patient's jawbone. In this way, the securing screw may be used to help further secure the base member to the patient's jawbone. In turn, this helps to stabilize the implant screw and the prosthesis that will be coupled to the implant screw.

In one aspect, the central opening is tapered and has a beveled edge. Also, the implant screw has a tapered head section to seat within the tapered central opening. This particular configuration is also useful in preventing microleakage between the base member and the implant screw.

In another aspect, the base member is generally rectangular in geometry, and the securing hole is located in a corner of the base member. In one particularly useful arrangement, the base member has two securing holes for use with two securing screws. The securing holes are located in opposing corners of the base member. Also, the securing holes may have a tapered section and the heads of the securing screws may have a tapered section. Further, the securing screws may each have a pointed end and a diameter of about 1.5 mm.

In a further aspect, the base member includes a plurality of retention grooves that are located on the outer periphery. Also, the outer periphery of the base member may taper inward from the top surface to the bottom surface such that the top surface is greater in surface area than the bottom surface. With this arrangement, the taper may begin below retention grooves. Additionally, the outer periphery of the base member is roughened to facilitate bone growth.

The system may be used with various prosthesis. For example, a crown may be mounted to the head of the implant screw. In some cases, the top side of the base member may includes at least one matable feature, and the crown may also include a corresponding matable feature that mates with the feature on the base member to non-rotationally secure the crown to the base member. The implant screw may include a threaded hole and the crown may include a bolt so that the bolt may be screwed into the threaded hole.

In yet another embodiment, the invention provides a platform for securing a dental crown to a patient's jawbone. The platform comprises a base member that is adapted to be embedded within a patient's jawbone at a treatment site. The base member has a generally flat top side, a generally flat bottom side, an outer periphery, a central opening and a screw hole positioned between the central opening and the outer periphery. The central opening tapers inward with a constant taper from the top surface to the bottom surface and is configured to receive an implant screw. The top side may further include at least one table feature that is configured to mate with a corresponding feature on a crown to ensure non-rotatable alignment of the crown with the base member.

In one aspect, the outer periphery may include a plurality of retention grooves, and the outer periphery may taper with a straight taper inward from the retention grooves to the bottom surface such that the top surface is greater in surface area than the bottom surface. In another aspect, the base member may be generally rectangular in geometry, and the securing hole is located in a corner of the base member. Two or more securing holes and securing screws may also be used.

Figure 1:
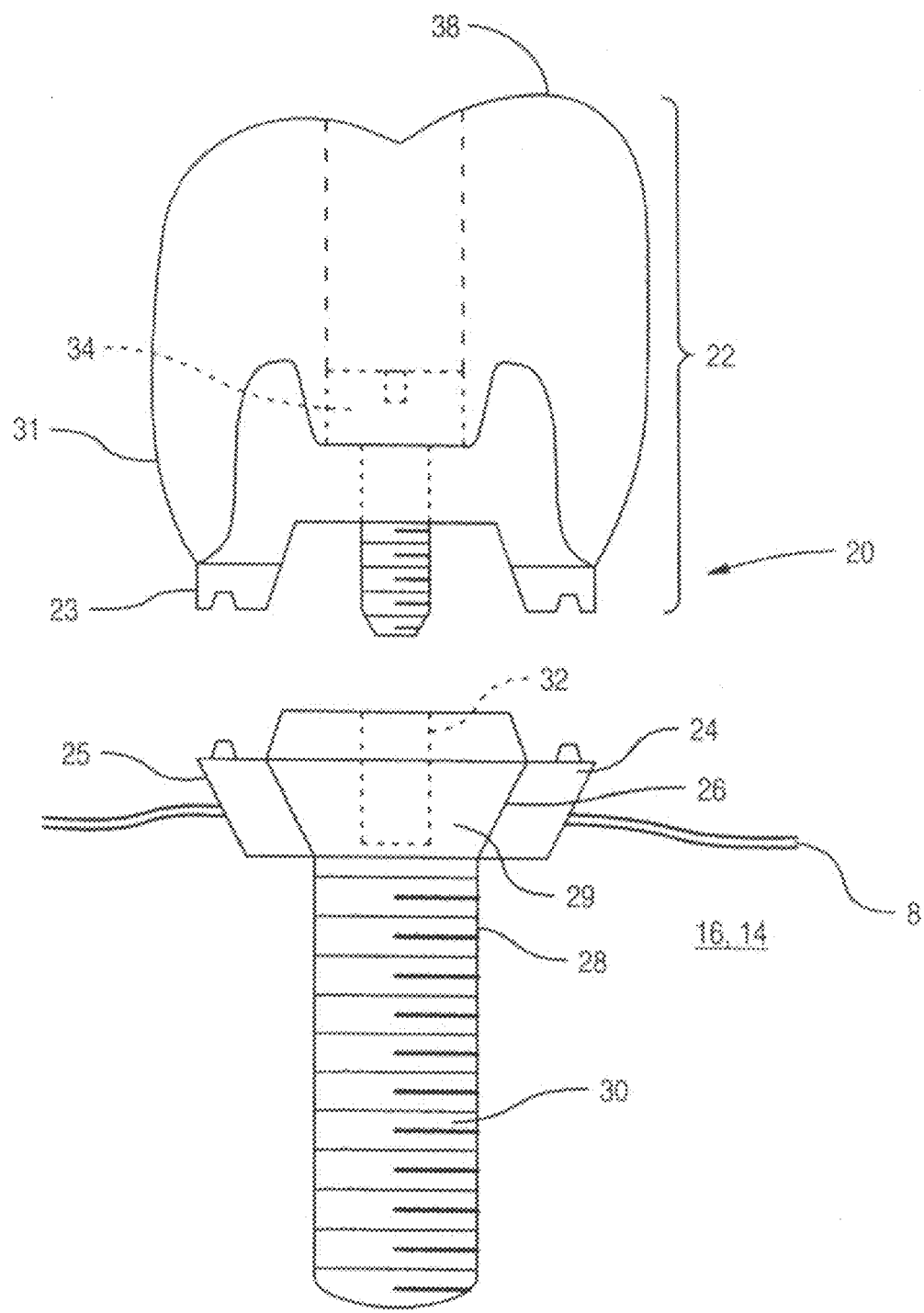
FIG. 1 is a side elevation diagram of an implant having an enlarged base seated directly on the jaw.

The following is a discussion and description of specific embodiments of this invention, such being made with reference to the drawings, wherein the some reference numerals are used to indicate the same or similar parts and/or structure. It should be noted that such discussion and description is not meant to unduly limit the scope of the invention.

DETAILED DESCRIPTION OF THE INVENTION

Restoring the edentulous space of missing first and second molars and bicuspids can be problematic. This is because these teeth are typically square or rectangular in geometry. Typical dental procedures restore this space using round dental implants. When the crown is placed onto the implant, there are excessive voids between the crown and adjacent teeth. These spaces serve as food traps and will eventually lead to tooth decay of the adjacent teeth. This problem generally arises because the implant is round yet is trying to fill a generally square or rectangular space.

One important feature of the invention is a way to provide a platform that generally fills this edentulous space so that when a square or rectangular crown is placed onto the implant there is minimal space between the crown and the adjacent teeth. The platforms of the invention are generally square or rectangular and are positioned about the implant to provide a convenient surface to attach the crown. In some cases, part of the patient's jawbone may be removed so that the platform may be countersunk within the patient's jawbone. In this way, when the crown is placed onto the platform not only will it be generally aligned with the adjacent teeth but the jawbone will tend to grow about the platform to provide a stable surface to support the crown.

A wide variety of platforms may be used in connection with most commercially available implants. Typically, the outer periphery of the platform will be generally rectangular or square and will have a central opening through which the implant may be inserted. The top surface of the platform is typically flat in geometry. However, it may include one or more detents or other features to mate with a corresponding feature on the crown and/or abutment so as to prevent rotation of the crown relative to the platform. Also, the platform may have one or more holes to permit small surgical screws to be inserted through the platform and into the jawbone so that the platform may be further secured to the patient's jawbone. These holes may be countersunk so that the surgical screws are generally flush with the top surface of the platform. The outer and bottom surfaces of the platform may have various grooves or roughened surfaces to facilitate bone healing and bone grown to the platform.

Once the platform is securely in place it essentially converts the round implant into a square or rectangular implant so as the match the outer geometry of the crown. In this way, voids or spaces between adjacent teeth are minimized to prevent decay and tooth loss that may otherwise result from the placement of the implant and crown.

FIG. 1 is a side elevation diagram of an improved tooth implant assembly 20 having a base 24 for seating on jaw 16. In one embodiment, tooth implant assembly 20 includes base plate 24, a base attachment fastener 28 (also referred to as an implant screw or simply an implant), a crown attachment fastener 34, a crown supporting mechanism 36 (FIG. 2), and a tooth crown 38.

Generally, the tooth implant assembly 20 comprises: i) a crown portion 22 having a lower portion 23 adapted for seating and connection; ii) base 24 having an upper portion adapted to matably receive the crown portion 22, a lower portion adapted to seat directly on (or be embedded within) the bone 14 of one of the jaws 16, the base 24 having an upright, or central, opening 26 therethrough; and, iii) a base attachment fastener 28 having a head 29 adapted to be seated o and around upright opening 26, and a threaded end portion, or shaft, 30 for screwable reception in the jaw 16 to thereby anchor the base 24 thereon. The base 24 of the implant 20 is enlarged to better distribute load on the jaw 16 and thereby additionally allow said crown portion 22 to have more upright peripheral sidewalls 31, so that embrasures, or periodontal gaps, 12 (FIGS. 3-7) between the bottom portion of the crown portion and adjacent teeth 10 (FIGS. 3-7) are thereby substantially reduced, and so that both food impaction and collection therein is also substantially reduced. In one embodiment, the base 24 is generally rectangular and non-rotatable.

Base attachment fastener 28 is adapted for insertion into and engagement with central opening 26 in base plate 24. In one embodiment, base attachment fastener 28 is a bone screw.

Head 29 of base attachment fastener 28 has a central bore 32 formed longitudinally in the body of fastener 28. In one embodiment, central bore 32 of base attachment fastener 28 extends into threaded shaft 30. In one embodiment, head 29 of base attachment fastener 28 is a countersink head adapted to fit countersunk central opening 26.

Within this specification "jaw" 16 is intended and defined to include either the upper jaw or the lower jaw. Similarly, within this specification "bone" 14 is intended and defined to include either the maxilla or the mandible.

If base 24 is sized generally similarly to the bottom portion of a removed tooth (not shown) then the periodontal gaps 12 on opposite sides of the implanted crown portion 22 will not be enlarged. The base 24 may be further enlarged to maximally minimize the periodontal gaps 12 between the implant 20 and adjacent teeth 10.

In one embodiment of the invention, the base 24 has a sloping peripheral sidewall 25 and the bottom side portion is smaller in area than the top side portion. The bottom side portion of the base 24 may be embedded within the bone 14 of the jaw 16. This may be done by removing a piece of the patient's jawbone prior to adhering base 24 to the jawbone. Alternatively, if bone 14 strength is an issue, the bottom side portion of the base 24 may be generally fitted to the vertical curvature of the bone 14 of the jaw 16.

In another embodiment of the invention, the peripheral sidewall 25 of the base 24 is coated or roughened to facilitate gum 8 adhesion thereto. In one embodiment, the upper portion of the base attachment screw 28 comprises an internally threaded hole, or central bore, 32 for reception of a crown attachment bolt 34. It is also contemplated that the top portion of the base 24 and the bottom side portion of the crown 22 are matingly configured to ensure proper and non-rotatable alignment of the crown portion 22 on the base 24.

Figure 2:
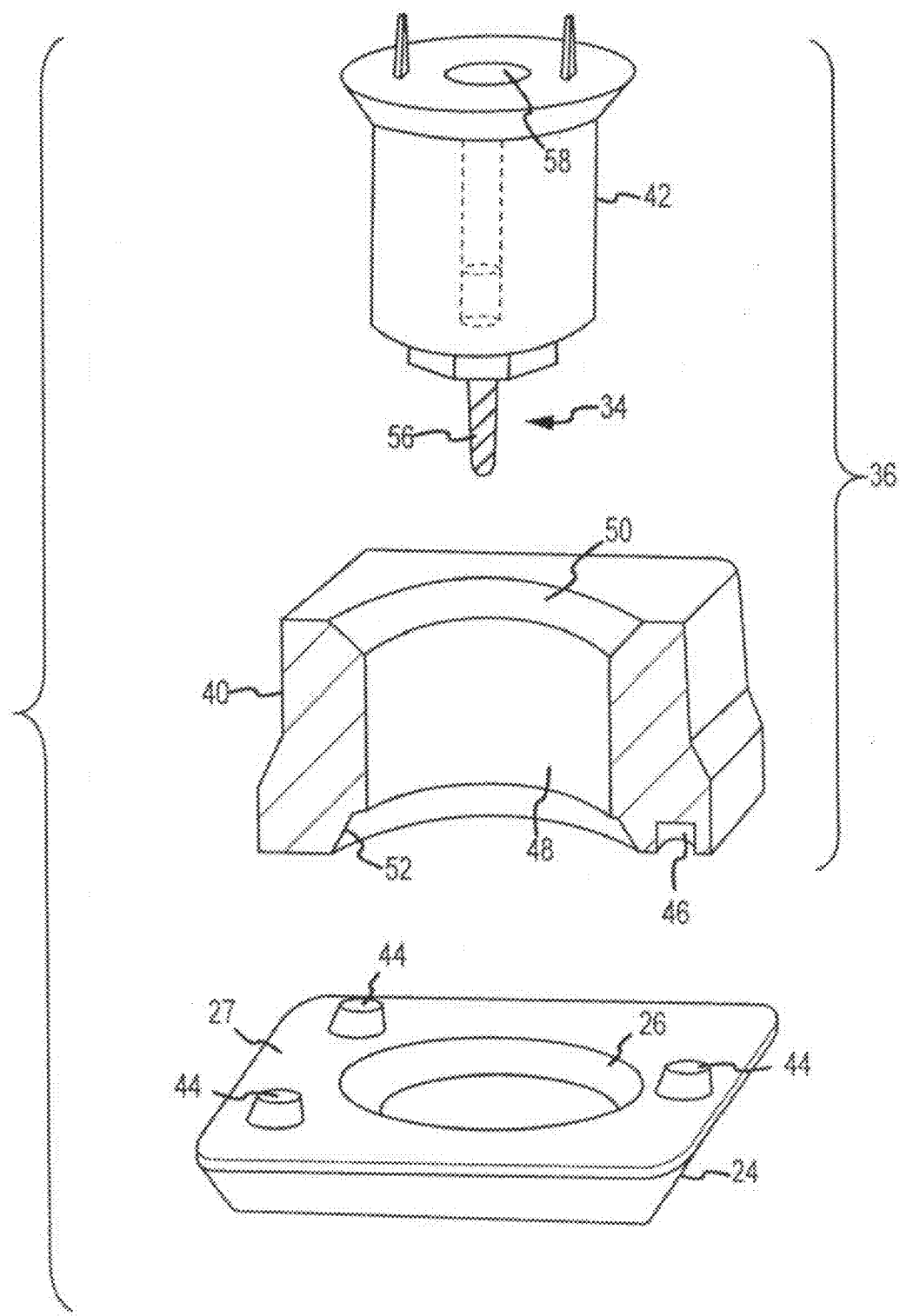
FIG. 2 is an exploded view of the base plate and crown supporting means of the implant.

FIG. 2 is a more detailed illustration of the base plate 24 and crown support mechanism 36 of implant 20. Tooth crown 38 is supported by and attached to crown supporting means 36. Together tooth crown 38, crown supporting mechanism 36, and crown attachment screw 34 embody crown portion 22.

Base plate 24 has central opening 26 and coronal surface 27. The terms "coronal" and "apical" are used in this specification to describe the side of a structure closest to the crown apex (root), respectively, of a tooth.

In one embodiment, central opening 26 of base plate 24 is countersunk. Central opening 26 may be beveled at any angle, even a concave angle, or it may be straight with no bevel. In one embodiment, coronal surface 27 is a flat surface. In one embodiment, coronal surface 27 of base plate 24 includes teeth means 44 for engagement, such as a plurality of upstanding studs 44.

Crown supporting mechanism 36 carries crown attachment fastener 34. Crown supporting mechanism 36 is disposed on coronal surface 27 of base plate 24. In one embodiment, crown support mechanism 36 includes recessions 46 for engaging detents 44 (also referred to as upstanding studs) of coronal surface 27. Of course, it will be appreciated that the recessions and detents may be on opposite parts or intermixed between the two parts.

In one embodiment, crown support mechanism 36 includes a collar 40 (also referred to as an abutment collar) and a cylindrical insert 42. Collar 40 is shown partially cut away in FIG. 2. Collar 40 includes longitudinal opening 48 with coronal 50 and apical 52 edges. Collar 40 is disposed on coronal surface 27 of base plate 24.

Cylindrical insert 42 is disposed within collar 40 and supported by coronal edge 50 of collar 40. Cylindrical insert 42 has a longitudinal channel 58 formed therein for carrying crown attachment fastener 34.

Crown attachment fastener 34 is adapted for threaded engagement with central bore 32 of base attachment fastener 28. In one embodiment, crown attachment fastener 34 has a threaded shaft 56 adapted for threaded engagement with central bore 32.

It will also be appreciated that any one of a variety of commercially available prosthesis may be coupled to implant 30 as is known in the art. As such, the invention is not limited to a specific crown attachment fastener, collar abutment, or prosthesis. Rather, embodiments of the invention provide a way to stabilize the implant screw and prosthesis using a stabile base or platform that is secured to the bone.

Generally, the method of implanting a tooth implant or prosthesis 20 in a jaw 16 comprises the following steps that do not necessarily need to proceed in order. The method utilizes a tooth implant 20, such as the one generally described above. A pilot hole 6 is drilled in the jawbone and is sized to accommodate the internal diameter of the base attachment screw 28. The hole 6 is laterally centered in the jaw 16 between adjacent teeth 10 in a open space left by a removed tooth (not shown). Sufficient gum 8 is removed to allow the base 24 to seat directly on the bone 14 of the jaw 16. Optionally, a portion of the jawbone may be removed so that base 24 may sit within the jawbone and be flush with the top surface. Once the treatment site is surgically prepared, the threaded end portion 30 of the base attachment screw 28 is positioned through the upright opening 26 in the base 24 and screw 28 is screwed into the bone 14 of the jaw 16 thereby attaching the base 24 to the jaw 16. As described hereinafter, base 24 may first be secured to the patient's jawbone by using one or more smaller screws that extend through the base and into the jawbone. These may be located, for example, between the central opening of base 24 and its outer perimeter. With base 24 secured and screw 28 in place, the surgeon may position, fit and maintain the removed gum 8 peripherally around the base 24 that is now attached to the jaw 16. A crown portion 22 may be molded and may have a bottom portion sized to fit on the base 24 and a top portion sized appropriately to fill the open space between the adjacent teeth 10. The molded crown portion 22 may be attached to the base 24 that is anchored on the jaw 16. The base 24 of the implant 20 is enlarged to better distribute load on the jaw 16, so that periodontal gaps 12 between the bottom portion of the crown portion 22 and adjacent teeth 10 are thereby reduced, and so that both food impaction and collection therein is minimal. This most general method may be detailed with the apparatus limitations specified above under the most general description of the tooth implant 20.

FIGS. 3-7 illustrate an embodiment for installing a tooth implant in a jaw 16 having bone 15 and gum 8. Although the steps represented in FIGS. 3-7 are presented in a specific order, the technology presented herein can be performed in any variation of this order. Furthermore, additional steps may be executed between the steps illustrated in FIGS. 3-7.

Figure 3:
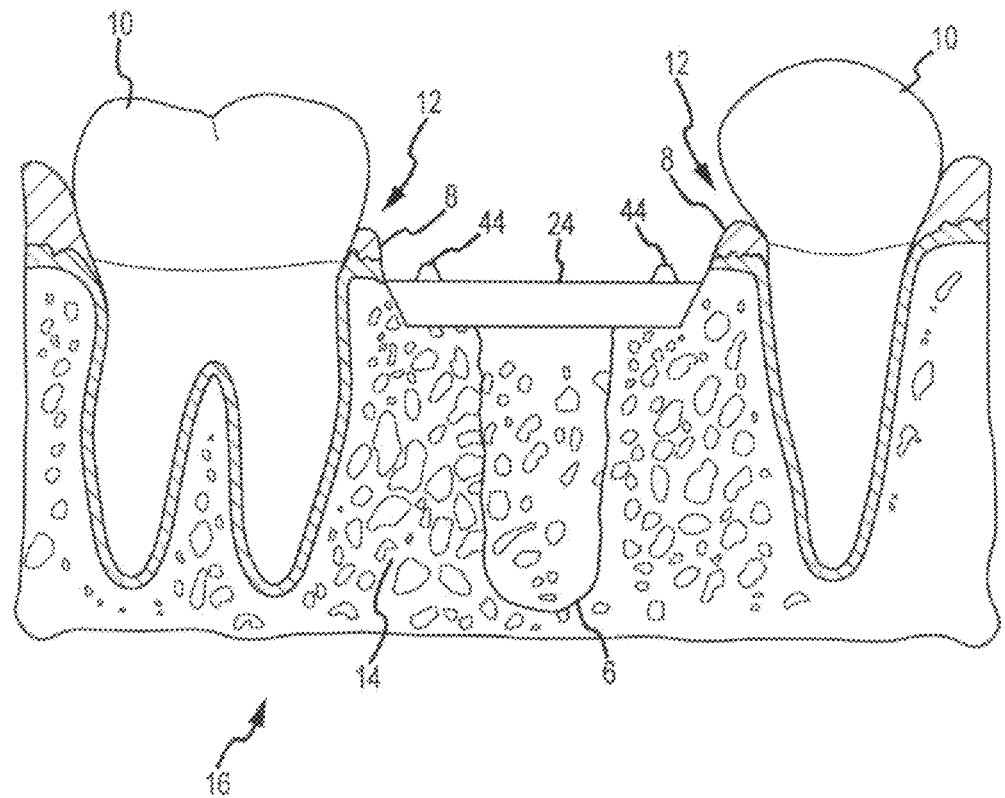
FIGS. 3-7 illustrate an embodiment of steps in a method for installing the tooth implant of FIG. 1.
Figure 4:
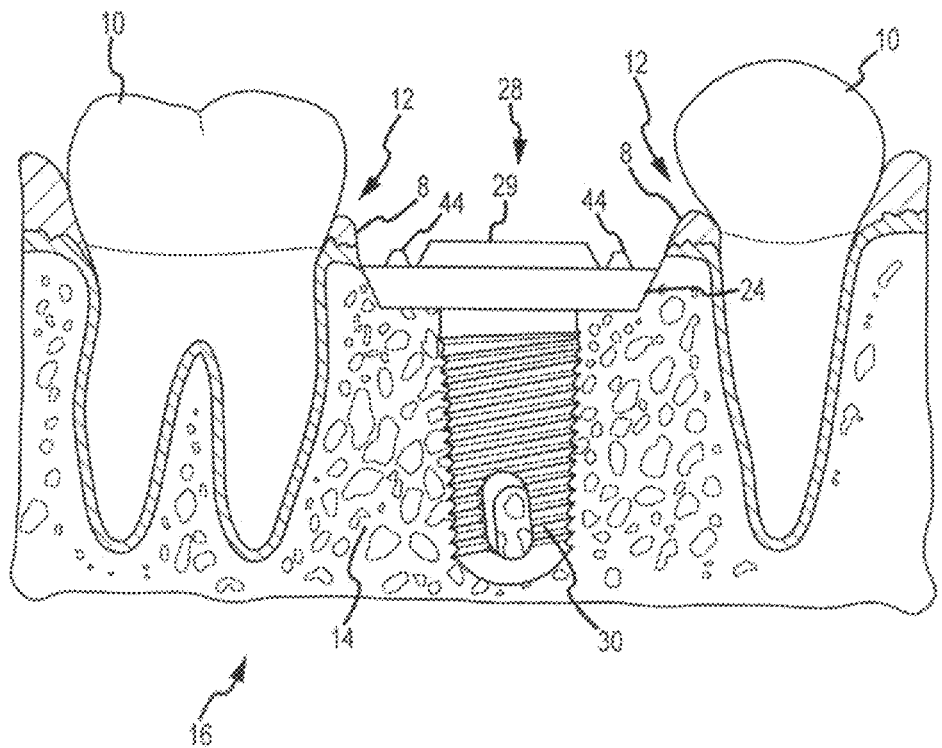
Figure 5:
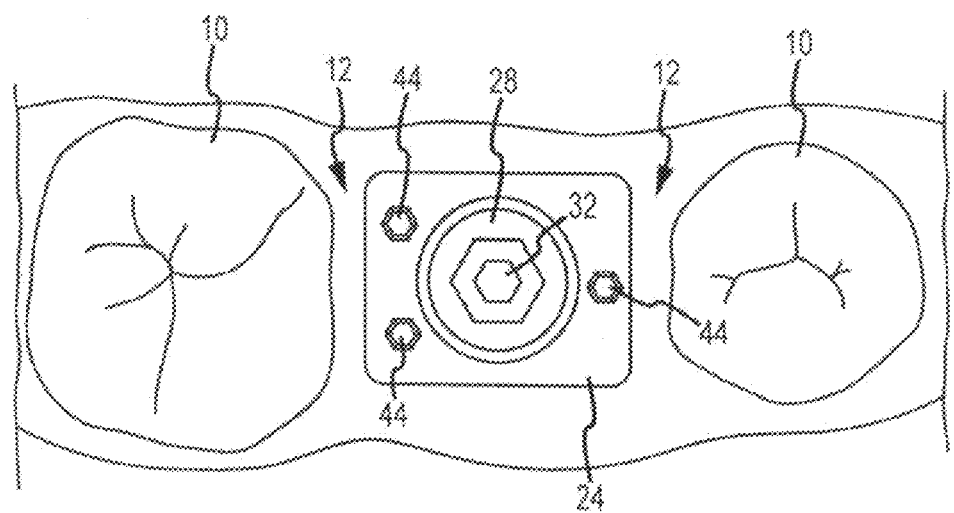

FIGS. 3 and 4 are side elevations of base plate 24 being fastened to jaw 16. FIG. 5 is a top elevation of the step shown in FIG. 4. In one embodiment, fastening base plate 24 to jaw 16 includes drilling a pilot hole 6, removing gum 8 and or bone 14 from jaw 16, and positioning threaded shaft 30 of base attachment screw 28 through central opening 26. Typically, enough bone may be removed so that the top surface of base plate 24 is flush with the top of bone 14. Although not shown, base plate 24 may include one or more through holes through which small surgical screws may be used to secure base plate 24 to bone 14. This may be done prior to or after inserting attachment screw 28.

Pilot hole 6 is typically sized to accommodate the internal diameter of base attachment screw 28. Pilot hole 6 is laterally centered in jaw 16. Also, sufficient gum 8 is removed from jaw 16 to allow base plate 24 of implant 20 to seat directly on bone 14 of jaw 16 (in cases where no bone is removed). Threaded shaft 30 of base attachment screw 28 is positioning through central opening 26 in base 24 of implant 20. Screw 28 is screwed into bone 14 of jaw 16 thereby attaching base plate 24 to jaw 16.

Figure 6:
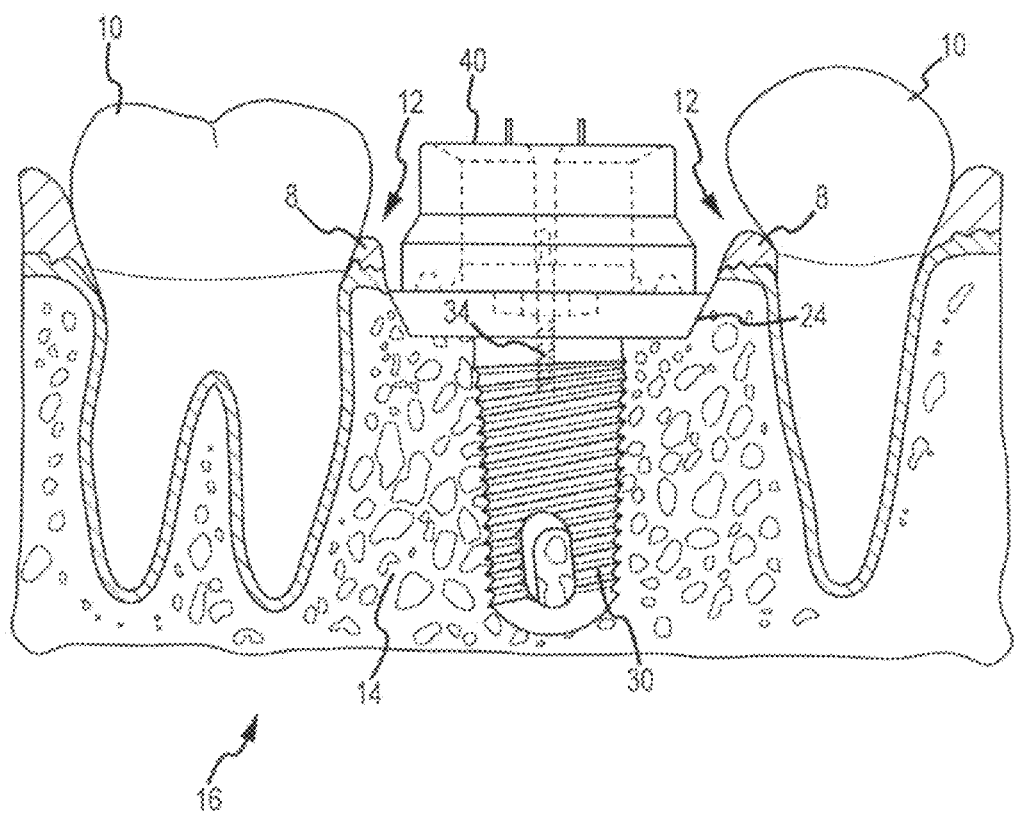
Figure 7:
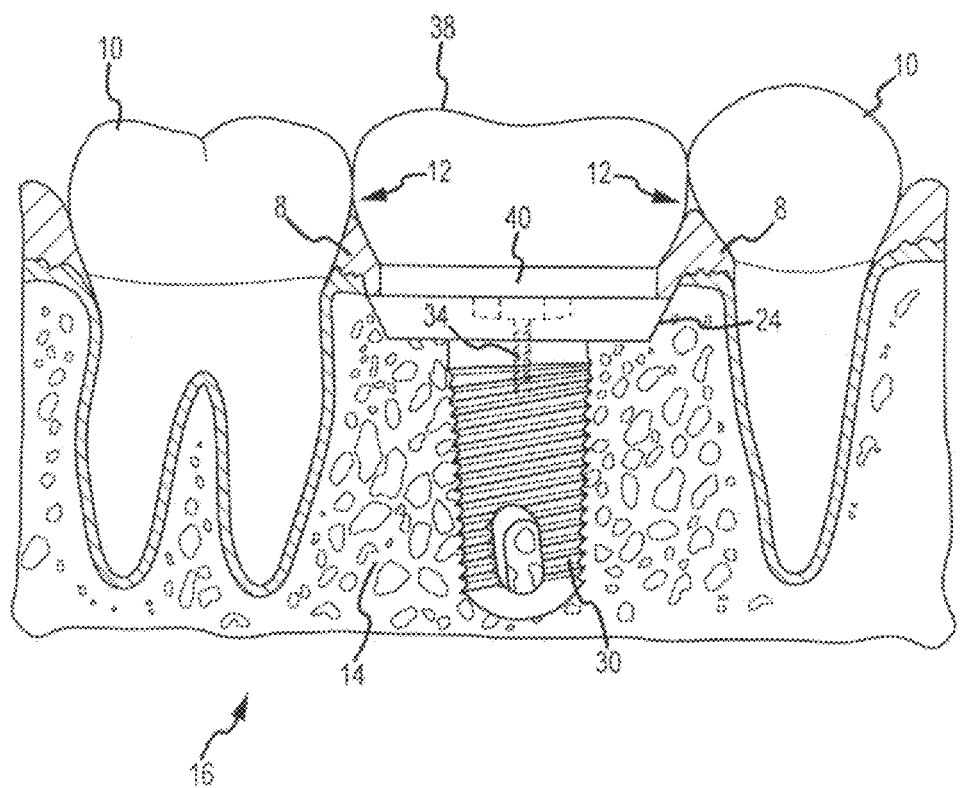

FIG. 6 is a side elevation showing cellar 40 being affixed to base plate 24. Longitudinal opening 48 is provided in collar 40. Collar 40 is disposed on coronal surface 27 of base plate 24. Crown attachment fastener 34 is inserted through collar 40. Cylindrical insert 42 is disposed within collar 40. FIG. 7 is a side elevation showing tooth crown 38 being attaching to collar 40.

Figure 8:
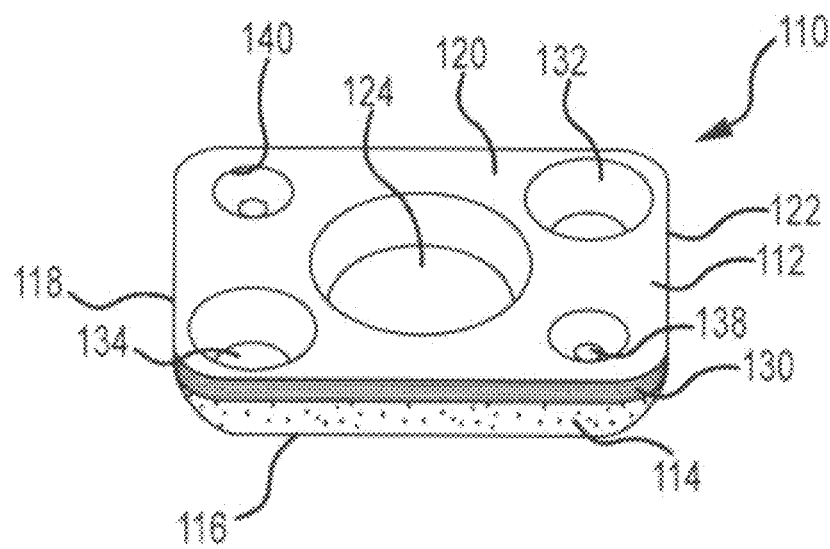
FIG. 8 is a top perspective view of one embodiment of a platform or base according to the invention.
Figure 9:
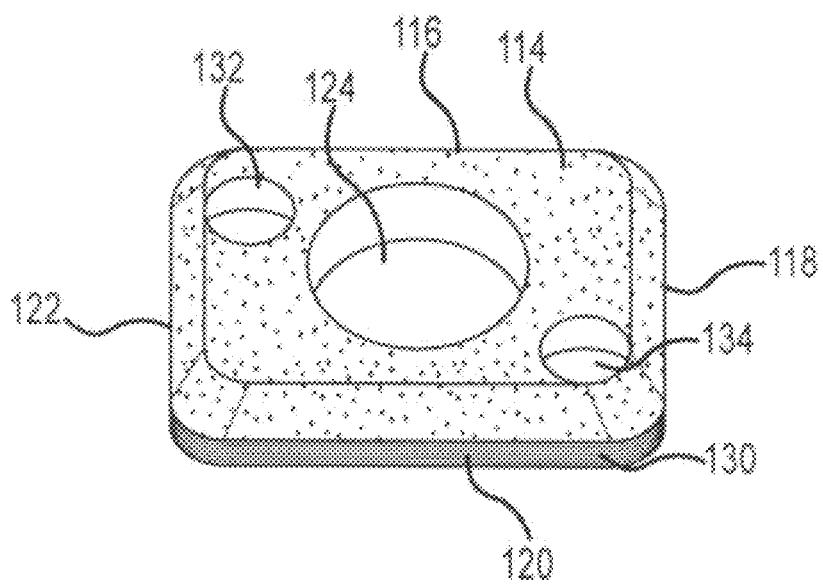
FIG. 9 is a bottom perspective view of the base of FIG. 8.

Referring now to FIGS. 8 and 9, one exemplary embodiment of a base 110 will be described. Base 110 is constructed of a stable material, such as polished titanium, ceramics, zirconia, or the like. Base 110 has a generally flat top surface 112 and a bottom surface 114. Base 110 also has four outer edges or sides 116, 118, 120 and 122. Formed in the center of base 110 is a central opening 124 through which an implant is inserted. Central opening 124 is beveled or tapered so that it generally matches the shape of the head of the implant. This tapering also assists to provide microleakage between base 110 and the implant.

Base 110 is generally square or rectangular in geometry and may have rounded corners. Typically, the length of sides 116 and 120 will be in the range of about 7 mm to about 12 mm, and more typically from about 8 mm to about 12 mm. The length of the opposing sides 118 and 122 may be in the range from about 5 mm to about 10 mm, and more particularly from about 6 mm to about 9 mm. The thickness of base 110 between top 112 and bottom 114 will typically be about 1 mm to about 4 mm, and more typically from about 2 mm to about 3 mm. Also, sides 116, 118, 120 and 122 may be angled from top 112 to bottom 114. Such angling of the sides is particularly useful for directing chewing force into the platform and bone and transferring it to the center implant to evenly disperse the load. Also, the sides and bottom 114 may be roughened to facilitate bone integration. For example, a pressure blasted aluminum oxide micro etching process may be used. Other processes include acid etching or other techniques to increase the surface area of the sides and the bottom. Also, grooves 130 may be placed on the sides of base 110 to also increase surface area and facilitate bone integration.

Also extending through base 110 are a pair of screw holes 132 and 134. These screw holes are also beveled or tapered to permit small surgical screws to be inserted through these holes and be flush with the top surface 112. These small screws extend into the patient's jawbone and serve to secure base 110 to the patient's jawbone. As shown, base 110 includes two screw holes which are located at opposing corners of the base. However, it will be appreciated that different numbers of screw holes could be used. For example, base 110 could be constructed with only a single screw hole. Alternatively, it could employ three screw holes, with two being in adjacent corners and one being on the opposite side. As another option, four screw holes could be employed, with the four holes being located in each of the corners.

Base 110 also includes two detents or dimples 138 and 140 in top surface 112. These dimples are designed to receive mating features on the abutment to prevent rotational movement of the abutment relative to base 110 once the abutment is secured to the implant. Although shown with dimples, it will be appreciated that other types of non-rotational features may be used. For example, bumps or ridges could be included on top surface 112 to mate with detents or dimples on the abutment. Also, any number of such non-rotational features could be employed.

Figure 10:
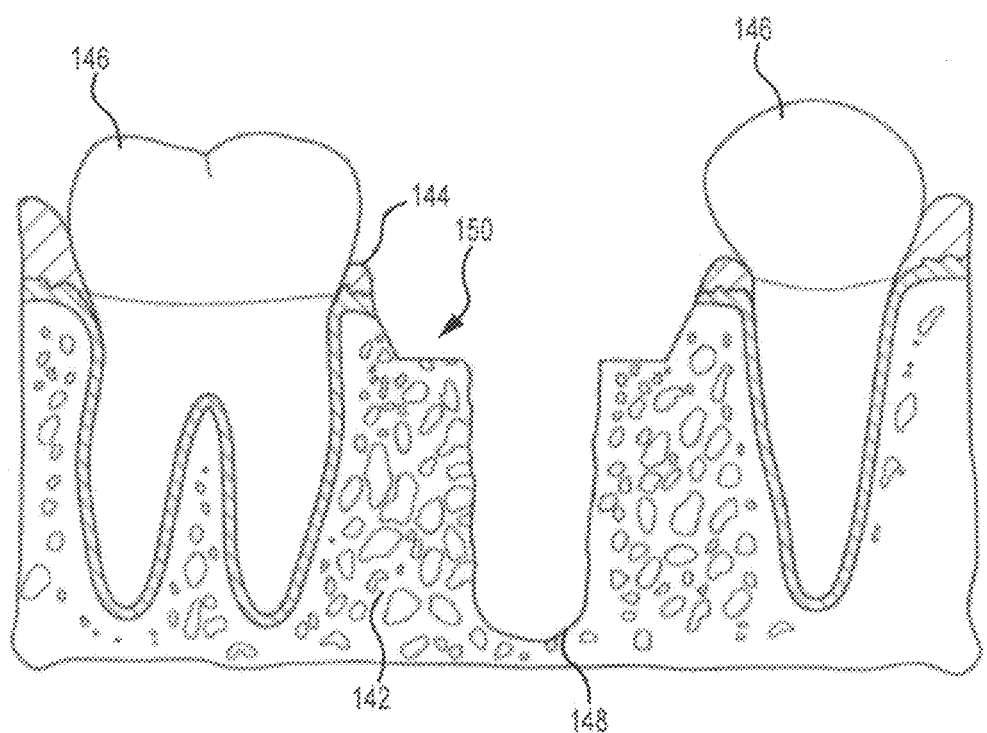
FIG. 10 illustrates a cross-sectional side view of a patient's jawbone that has been drilled to receive an implant and in which a rectangular portion has been surgically removed in order to receive a base according to the invention.
Figure 11:
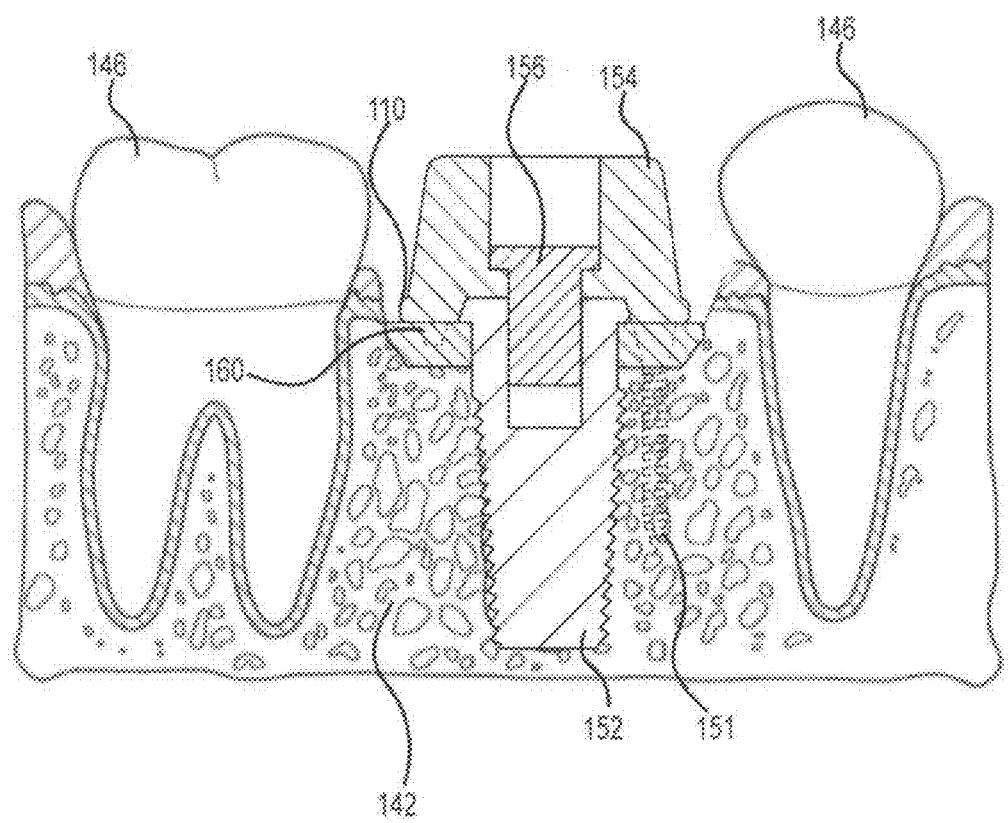
FIG. 11 illustrates an implant that has been inserted into the jawbone of FIG. 10 with a corresponding base and abutment.
Figure 12:
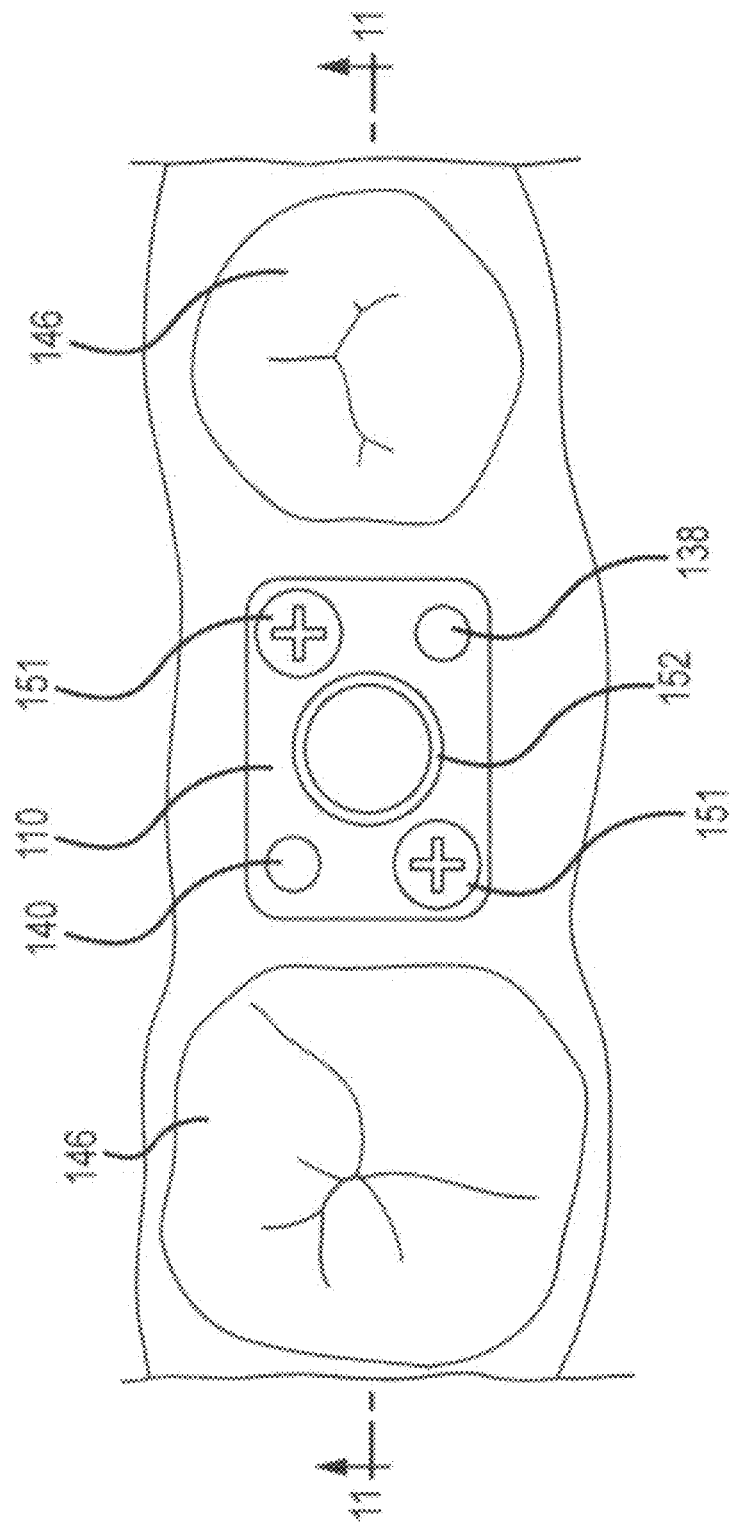
FIG. 12 is a top view of the base and implant of FIG. 11 prior to attachment of the abutment.

FIG. 10 illustrates a cross-sectional view of a patient's jawbone prior to placement of base 110 or an implant. In FIG. 10, the patient's jawbone is illustrated by reference numeral 142 and the tissue or gum line above the patient's jawbone is illustrate by reference numeral 144. As shown, one tooth has been removed leaving a space or void between adjacent teeth 146. Prior to placement of an implant or a base, an appropriate hole 148 is drilled and a generally square or rectangular recess 150 is cut into the patient's jawbone. As illustrated in FIG. 11, base 110 has been secured within recess 150. The sides 116, 118, 120 and 122 generally match with the outer sides or walls of recess 150 while bottom 114 rests upon the removed portion of the jawbone. To secure base 110 in place, screws 151 have been inserted through screw holes 132 and 134 (see FIG. 8) and into the jawbone. Screws 151 will typically have a length in the range from about 5 mm to about 11 mm, and more typically from about 7 mm to about 9 mm. In this way, base 110 is secured to the patient's jawbone 142. Top surface 112 is generally flush with the top of the patient's jawbone so that it essentially functions as part of the patient's jawbone. A more detailed view of screws 151 that secure base 110 to the patient's jawbone is illustrated in FIG. 12.

Once base 110 is securely in place, an implant 152 is screwed into the opening 148 until the head of the implant is seated within central opening 124. At this point, a screw or healing cap may be inserted into the top end of implant 152 and remain in place for several weeks until bone has properly healed and adhered to base 110. The healing cap may then be removed so that an abutment 154 (see FIG. 11) may be secured to base 110. For example, a hex 156 may be screwed through a central opening of abutment 154 and into implant 152. Also, bumps 160 on the undersurface of implant 154 mate with detents 138 and 140 on base 110 to prevent rotational movement of abutment 154 relative to base 110. Once abutment 154 is securely in place a prosthesis, such as a crown, is secured to abutment 154. The outer shape of abutment 154 is generally square or rectangular in geometry and therefore matches the outer shape of base 110 and tapers outward from a top end to a bottom end such that an outer periphery of the top end is smaller than the outer periphery of the bottom end. In this way, voids or gaps between the crown that is placed on abutment 154 and the adjacent teeth 146 is minimized. Typically, the outer edges of abutment 154 will come within about 1 mm to about 4 mm of side walls 116, 118, 120 and 122. This provides sufficient space for the resulting crown that will be placed on lop of abutment 154.

Figure 13:
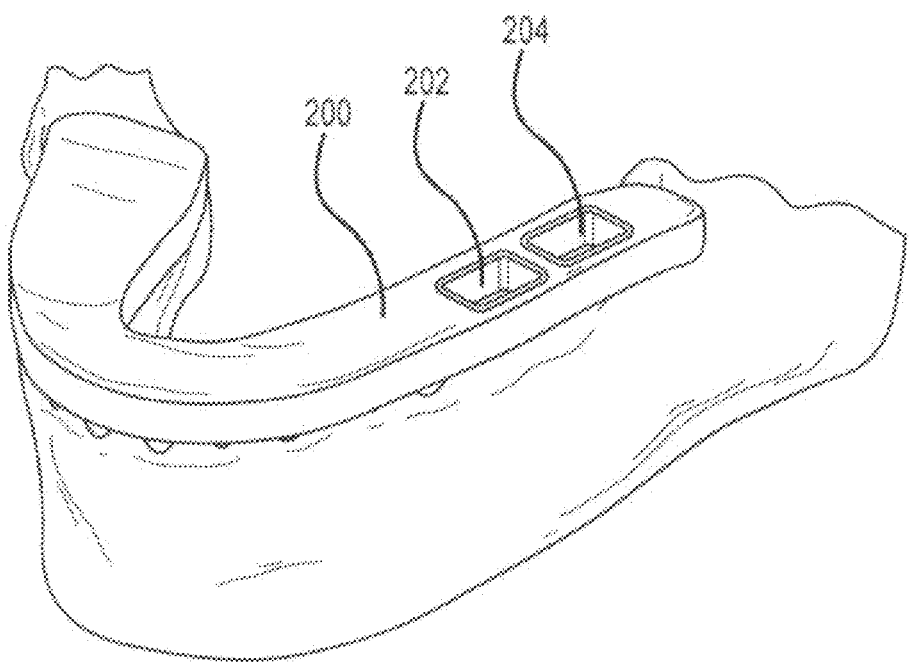
FIG. 13 is a perspective view of a template that may be employed when surgically removing portions of the patient's jawbone according to the invention.

FIG. 13 is a perspective view of a template 200 that may be used when surgically producing the sites needed for placement of an implant and base as described in previous embodiments. Template 200 is molded so that it fits over the patient's teeth. Also, template 200 has two through holes 202 and 204 that serve as guides when removing the patient's jawbone at a treatment site. Although shown with two through holes, it will be appreciated that any number may be used depending on the number of implant sites. Through holes 202 and 204 are specifically aligned with where the patient's removed teeth were previously located. In this way, when a surgical device, such as a hand-held router, is directed through the through holes 202 and 204, it produces a rectangular recess in the patient's jawbone.

Figure 14:
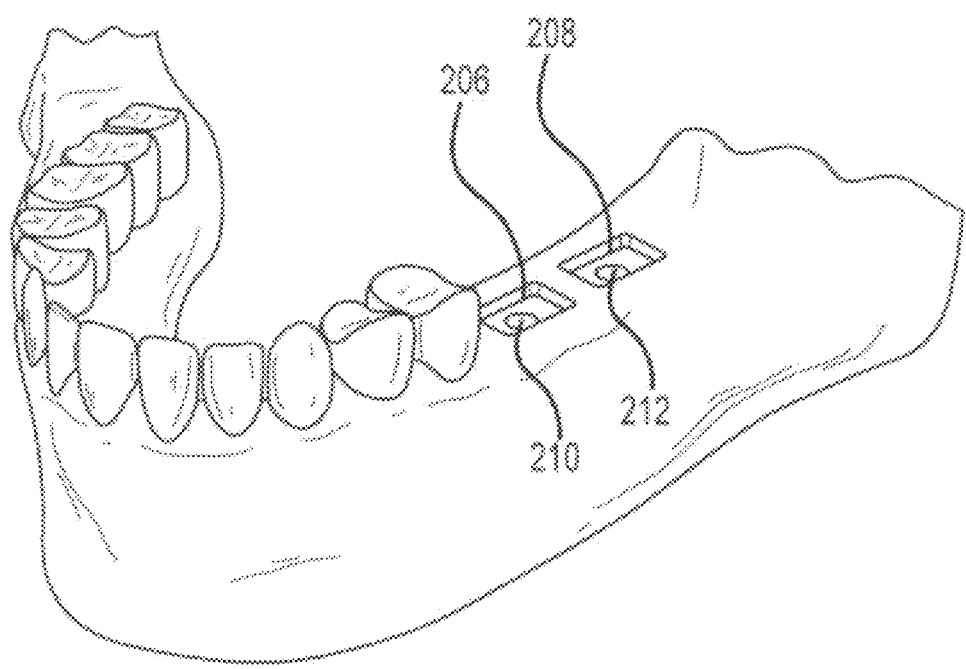
FIG. 14 illustrates the surgical recesses tented within the patient's jawbone using the template of FIG. 13.

FIG. 14 illustrates the recesses 206 and 208 that are formed within the patient's jawbone when using template 200 of FIG. 13. Also shown are two holes 210 and 212 that have been drilled to receive the implant. Above holes 210 and 212 are the rectangular recesses 206 and 208 in the jawbone which are sized to receive bases or platforms as described herein.

Figure 15:
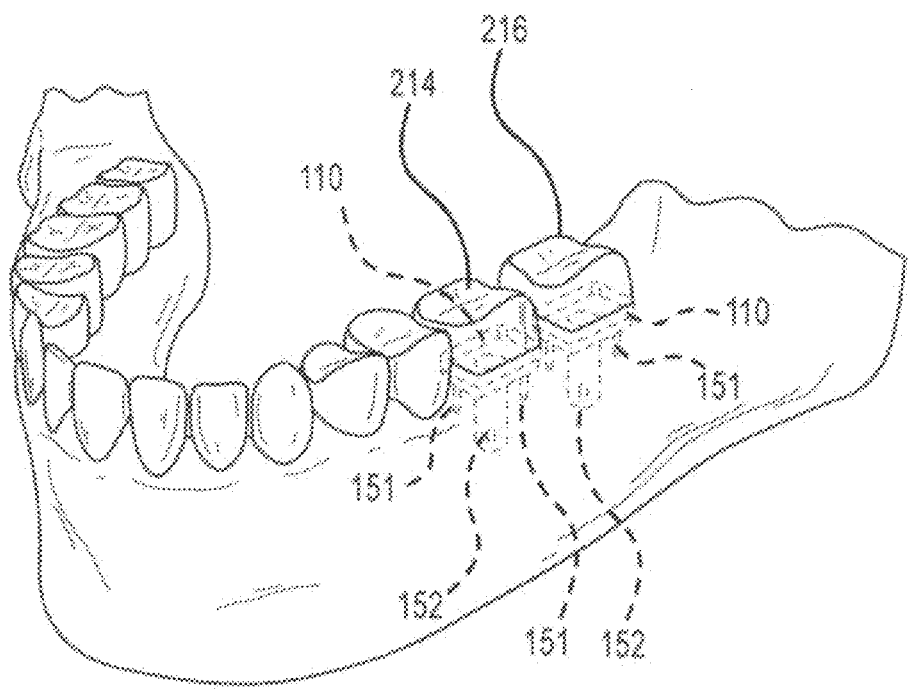
FIG. 15 illustrates crowns that have been restored to the surgical sites of FIG. 14 according to the invention.

FIG. 15 illustrates in phantom line the implants 152, bases 110 and surgical screws 151 previously described in connection with FIG. 11. Also positioned on top of each base is a crown 214 and 216. Not shown in phantom line for convenience of illustration are the abutments that sit between the crowns and the base. As the space between each crown and/or adjacent tooth is minimized by the nature of the rectangular bases. In this way, the amount of food or other material that may be potentially trapped between two adjacent teeth and/or crowns is minimized.

The foregoing description is only illustrative of the invention and not intended to be exhaustive or to limit the invention to the precise forms disclosed. Various alternatives and modifications can be devised by those skilled in the art without departing from the invention. Accordingly, the present invention embraces all such alternatives, modifications, and variances that fall within the scope of the appended claims.

What is claimed is:

1. A method for securing a dental implant to a patient's jawbone, the method comprising:
    removing a portion of the patient's gum at a treatment site sufficient to expose the patient's jawbone;
    removing a portion of the patient's jawbone at the treatment site to form a generally square or rectangular recess in the patient's jawbone;
    positioning a base member at the treatment site such that the base member is embedded within the patient's jawbone at the treatment site, wherein the base member has a generally flat top side defined by an outer periphery, a tapered central opening and at least one screw hole positioned between the central opening and the outer periphery and wherein the outer periphery is generally square or rectangular in geometry;
    inserting a securing screw through the screw hole;
    rotating the securing screw until the securing screw is screwed into the patient's jawbone and a head of the securing screw is at least flush with the top side of the base member;
    inserting an implant screw through the central opening, wherein the implant screw has a head with a tapered section and a threaded end;
    turning the implant screw to secure the threaded end within the jawbone and to seat the head of the implant screw within the tapered opening of the base member;
    securing an abutment to the base member, wherein the abutment comprises a top end and a bottom end having an outer periphery that is generally square or rectangular in geometry so as to match the shape of the outer periphery of the base member, wherein the abutment tapers outward from the top end to the bottom end such that an outer periphery of the top end is smaller than the outer periphery of the bottom end,
    and wherein an outer periphery edge of the bottom end of the abutment is inset from the outer periphery of the base member.

2. A method as in claim 1, wherein the base member includes two screw holes that are positioned between the outer periphery and the central opening, and further comprising inserting securing screws through each of the screw holes.

3. A method as in claim 2, wherein the screw holes are located in corners of the base member.

4. A method as in claim 1, wherein the top side of the base member is generally flush with the patient's jawbone, and wherein a distance of the inset in the range from about 1 mm to about 4 mm.

5. A method as in claim 1, wherein the top side further includes at least one matable feature that is configured to mate with a corresponding feature on the abutment to ensure non-rotatable alignment of the abutment with the base member, and further comprising attaching the abutment to the implant screw, wherein the abutment includes a corresponding matable feature that mates with the feature on the base member to non-rotationally secure the abutment to the base member.

6. A method as in claim 5, wherein the implant screw includes a threaded hole and the abutment includes a bolt, and wherein the bolt is screwed into the threaded hole.

7. A method as in claim 1, wherein the base member has a generally flat bottom side, wherein the central opening tapers inward from the top surface to the bottom surface with a constant taper, and wherein the outer periphery of the base member tapers with a straight taper inward from the top surface to the bottom surface such that the top surface is greater in surface area than the bottom surface.

8. A method as in claim 1, wherein the portion of the patient's jawbone that is removed forms a rectangular cavity in the patient's jawbone.

9. A method as in claim 1, wherein the treatment site is where a tooth previously existed, and wherein the base member is sized to be generally the same size as the removed tooth.

10. A method as in claim 1, wherein the outer periphery of the base member is roughened.

11. A dental implant system comprising:
    a base member that is adapted to be embedded within a patient's jawbone at a treatment site, wherein the base member has a generally flat top side defining an outer periphery, a bottom side, a central opening, and at least one screw hole positioned between the central opening and the outer periphery, and wherein the outer periphery is generally square or rectangular in geometry to permit the base member to be positioned within a generally square or rectangular recess in the patient's jawbone;
    an implant screw comprising a head and a threaded end, wherein the threaded end is adapted to pass through the central opening of the base member and into the patient's jawbone, and wherein the head is adapted to be seated within the central opening of the base member after the threaded end is screwed into the patient's jawbone;
    a securing screw that is smaller in size than the implant screw, wherein the securing screw comprises a head and a threaded end, wherein the threaded end is adapted to pass through the screw hole of the base member and into the patient's jawbone; and
    an abutment that is configured to be positioned atop the base member and to receive a crown, wherein the abutment comprises a top end and a bottom end having an outer periphery that is generally square or rectangular in geometry so as to match the shape of the outer periphery of the base member, wherein the abutment tapers outward from the top end to the bottom end such that an outer periphery of the top end is smaller than the outer periphery of the bottom end, and wherein an outer periphery edge of the bottom end of the abutment is insert from the outer periphery of the base member.

12. A system as in claim 11, wherein the threaded end of the securing screw is pointed.

13. A system as in claim 11, wherein the central opening is tapered and has a beveled edge, and wherein the implant screw has a tapered head section to seat within the tapered central opening.

14. A system as in claim 11, wherein the base member is generally rectangular in geometry, and wherein the securing hole is located in a corner of the base member.

15. A system as in claim 14, further comprising a second securing hole and a second securing screw.

16. A system as in claim 15, wherein the securing holes are located in opposing corners of the base member.

17. A system as in claim 11, wherein the securing hole has a tapered section and the head of the securing screw has a tapered section.

18. A system as in claim 11, wherein the securing screw has a diameter of about 1.5 mm.

19. A system as in claim 11, further comprising a plurality of retention grooves located on the outer periphery of the base member.

20. A system as in claim 19, wherein the outer periphery of the base member tapers inward from the top surface to the bottom surface such that the top surface is greater in surface area than the bottom surface, and wherein the taper begins below retention grooves.

21. A system as in claim 11, wherein the outer periphery of the base member is roughened.

22. A system as in claim 11, wherein the abutment is adapted to be mounted to the head of the implant screw, wherein the top side of the base member further includes at least one matable feature, wherein the abutment includes a corresponding matable feature that mates with the feature on the base member to non-rotationally secure the abutment to the base member.

23. A system as in claim 22, wherein the implant screw includes a threaded hole and the abutment includes a bolt, and wherein the bolt is screwed into the threaded hole.

24. A platform for securing a dental crown to a patient's jawbone, the platform comprising:
a base member that is adapted to be embedded within a patient's jawbone at a treatment site, wherein the base member has a generally flat top side, a generally flat bottom side, an outer periphery, a central opening and a screw hole positioned between the central opening and the outer periphery, wherein the central opening tapers inward with a constant taper from the top surface to the bottom surface and is configured to receive an implant screw, wherein the top side further includes at least one matable feature that is configured to mate with a corresponding feature on a crown to ensure non-rotatable alignment of the crown with the base member, wherein the base member is generally square or rectangular in geometry at the outer periphery, and wherein the outer periphery includes sides that extend perpendicular to the top side, then taper with a straight taper inward to the bottom surface such that the top surface is greater in surface area than the bottom surface, wherein the outer periphery is roughened.

25. A platform as in claim 24, wherein the roughened outer periphery includes a plurality of retention grooves on the sides.

26. A platform as in claim 24, wherein the screw hole is located in a corner of the base member.

27. A platform as in claim 24, further comprising a second screw hole.

28. A platform as in claim 27, wherein the screw holes are located in opposing corners of the base member.

* * * * *